United States Patent
Inagaki et al.

(10) Patent No.: US 6,343,499 B1
(45) Date of Patent: Feb. 5, 2002

(54) AIR-FUEL RATIO DETECTING APPARATUS AND METHOD

(75) Inventors: Shinsuke Inagaki, Toyota; Takahide Izutani; Keiichiro Aoki, both of Susono, all of (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/448,078

(22) Filed: Nov. 23, 1999

(30) Foreign Application Priority Data

Dec. 24, 1998 (JP) .......................... 10-367236

(51) Int. Cl.[7] .................. G01N 27/26; G01N 27/41; G01N 27/417
(52) U.S. Cl. .................. 73/23.32; 73/23.2; 123/688
(58) Field of Search .................. 73/23, 32, 23.2; 123/688

(56) References Cited

U.S. PATENT DOCUMENTS

| 4,121,548 A | * 10/1978 | Hattori et al. | 73/23.32 |
| 4,177,787 A | * 12/1979 | Hattori et al. | 123/688 |
| 5,852,228 A | * 12/1998 | Yamashita et al. | 73/23.32 |
| 5,967,129 A | * 10/1999 | Yamashita et al. | 123/688 |
| 5,974,857 A | * 11/1999 | Yamashita et al. | 73/23.32 |
| 6,205,989 B1 | * 3/2001 | Aoki | 123/688 |

FOREIGN PATENT DOCUMENTS

JP    8-271475    10/1996

* cited by examiner

Primary Examiner—Daniel S. Larkin
(74) Attorney, Agent, or Firm—Kenyon & Kenyon

(57) ABSTRACT

Under normal conditions, the temperature of an oxygen ion-conductive element provided in a sensor body is about 700° C., and the element impedance is about 30 Ω. If there is a fault in the sensor body or a sensor body drive circuit, the current becomes zero and the element impedance becomes infinite. If a heater has deteriorated, the element temperature rises only up to, for example, about 550° C., and the element impedance becomes about 150 Ω. If there is a fault in the heater or the heater drive circuit, the element is heated only by exhaust gas, so that the element temperature rises only up to about the temperature of exhaust gas and the element impedance becomes a value corresponding to an element temperature of about 300° C. Three reference values Z1, Z2, Z3 are set for comparison with the detected value of element impedance in order to perform fault diagnosis.

16 Claims, 10 Drawing Sheets

AIR-FUEL RATIO DETECTING APPARATUS AND METHOD

INCORPORATION BY REFERENCE

The disclosure of Japanese Patent Application No. HEI 10-367236 filed on Dec. 24, 1998, including the specification, drawings, and abstract thereof, is incorporated herein by reference in its entirety.

BACKGROUND OF THE INVENTION

1. Field of the Invention

The present invention relates to an air-fuel ratio detecting apparatus and method employing a limit current type air-fuel ratio sensor and, more particularly, to fault diagnosis of an air-fuel ratio detecting apparatus.

2. Description of the Related Art

In order to achieve both a reduced specific fuel consumption and a reduced amount of harmful gas emissions in a vehicular internal combustion engine, it is necessary to control the air-fuel ratio to be burned in the engine over a wide air-fuel ratio range. To enable such air-fuel ratio control, an air-fuel ratio sensor (generally termed full-range air-fuel ratio sensor, linear air-fuel ratio sensor, and the like) utilizing the occurrence of a limit current in accordance with an oxygen concentration or an unburned gas concentration in exhaust gas in response to application of a current to a sensor body provided by forming an atmospheric-side electrode, an exhaust-side electrode and an exhaust-side diffusion resistor in an oxygen ion-conductive element of, for example, a zirconia solid electrolyte or the like, is known. Air-fuel ratio feedback control based on outputs of such air-fuel ratio sensors is performed according to the conventional art.

Air-fuel ratio feedback control based on the output of a full-range air-fuel ratio sensor essentially requires that an active state of the oxygen ion-conductive element be maintained. Therefore, the conventional art performs a control in which the temperature of the oxygen ion-conductive element is kept constant by heating the element through the use of a heater. Although the element temperature is a necessary factor in this control, the need for a temperature sensor is eliminated by estimating an element temperature from a detected element resistance on the basis of a correlation between the element resistance and the element temperature.

It is a precondition for the use of the above-described air-fuel ratio sensor to perform fault diagnosis on the air-fuel ratio sensor and, if there is any abnormality, take an immediate measure. Japanese Patent Application Laid-Open No. HEI 8-271475, as for example, discloses a technology that detects an element resistance of an oxygen ion-conductive element and, if the element resistance is outside a predetermined range, determines that the oxygen ion-conductive element has an abnormality.

However, since the air-fuel ratio sensor is formed by sensor body, a sensor body drive circuit for driving the sensor body and detecting an output current thereof, and a heater and heater drive circuit for heating the sensor body to activate the oxygen ion-conductive element, it is necessary to consider a wiring break or the like in the sensor body drive circuit, a wiring break or the like in the heater or the heater drive circuit, deterioration of the heater, and the like.

SUMMARY OF THE INVENTION

Accordingly, it is an object of the invention to provide an air-fuel ratio detecting apparatus that is formed by an air-fuel ratio sensor and its peripheral circuits so as to be capable of performing fault diagnosis in a simple, easy, and accurate manner.

To achieve the aforementioned and other objects of the invention, an air-fuel ratio detecting apparatus in accordance with one aspect of the invention includes an air-fuel ratio sensor having a sensor body that generates a limit current in accordance with at least one of an oxygen concentration and an unburned gas concentration in a detection-object gas upon application of a voltage to the sensor body, a sensor body drive circuit that drives the sensor body, an element impedance detection device for detecting an element impedance of an oxygen ion-conductive element provided in the sensor body by applying an AC voltage to the sensor body, and a diagnostic device for, based on the element impedance detected by the element impedance detection device, determining whether there is a fault and diagnosing a fault.

In the air-fuel ratio detecting apparatus of the invention, if the element impedance is greater than a first reference value and is considered to be infinite, the diagnostic device may determine that there is a break in at least one of the sensor body and the sensor body drive circuit.

Furthermore, the air-fuel ratio detecting apparatus may further have a construction as follows. The air-fuel ratio sensor has a heater that heats the sensor body to activate the oxygen ion-conductive element. The air-fuel ratio detecting apparatus further includes a heater drive circuit that drives the heater. If the element impedance is smaller than the first reference value but greater than a second reference value, the diagnostic device determines that there is an abnormality in at least one of the heater and the heater drive circuit.

Still further, if the element impedance is smaller than a third reference value that is between the first reference value and the second reference value in terms of magnitude and the element impedance is greater than the second value, the diagnostic device may determine that the heater has deteriorated.

Further, if the element impedance is greater than a third reference value that is between the first reference value and the second reference value in terms of magnitude and the element impedance is smaller than the first value, the diagnostic device may determine that there is a break in at least one of the heater and the heater drive circuit.

Further, the diagnostic device may perform diagnosis when the oxygen ion-conductive element is in an active state.

Further, the diagnostic device may perform diagnosis when an internal combustion engine in which the air-fuel ratio sensor is installed is in an idle state.

Further, the element impedance detection device may detect the element impedance by applying a voltage obtained by superimposing an element impedance-detecting AC component on an air-fuel ratio-detecting DC component, to the sensor body, and measuring an AC component of an output current of the air-fuel ratio sensor.

BRIEF DESCRIPTION OF THE DRAWINGS

The foregoing and further objects, features, and advantages of the present invention will become apparent from the following description of a preferred embodiment with reference to the accompanying drawings, wherein like numerals are used to represent like elements and wherein.

DETAILED DESCRIPTION OF PREFERRED EMBODIMENT

A preferred embodiment of the invention will be described hereinafter with reference to the accompanying drawings.

Figure 1:
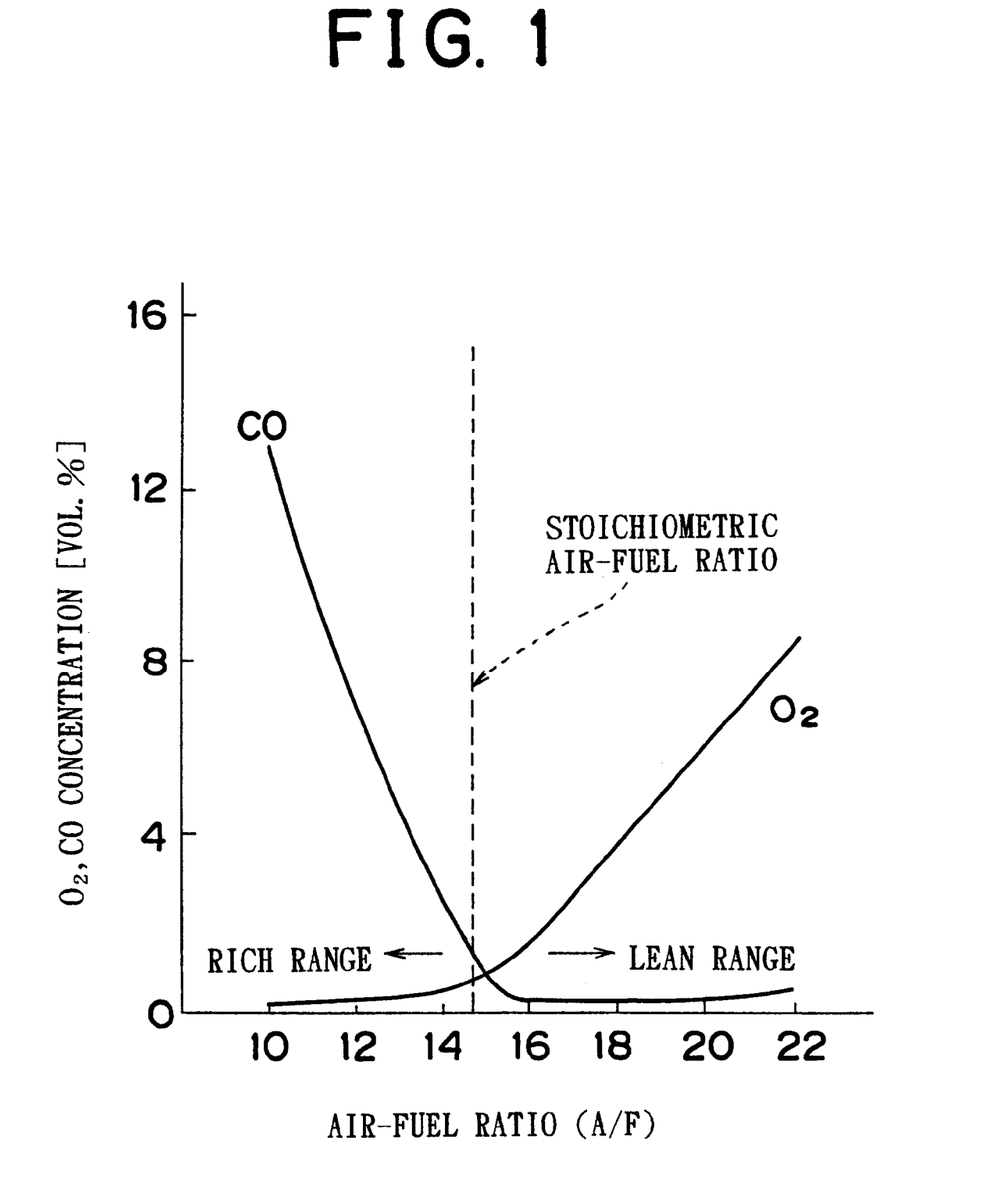
FIG. 1 is a characteristic graph indicating relationships between the air-fuel ratio and the exhaust gas concentrations.

The principle in an air-fuel ratio sensor will first be explained. FIG. 1 is a characteristic graph indicating a relationship between the air-fuel ratio and the oxygen ($O_2$) concentration in exhaust gas and a relationship between the air-fuel ratio and the carbon monoxide (CO) concentration in exhaust gas. As indicated by the graph, the $O_2$ concentration changes substantially linearly with the air-fuel ratio in a fuel-lean air-fuel ratio range. In a fuel-rich air-fuel ratio range, on the other hand, the concentration of CO, that is, an unburned gas, changes substantially linearly with the air-fuel ratio. The air-fuel ratio sensor utilizes these characteristics, as described below.

Figure 2:
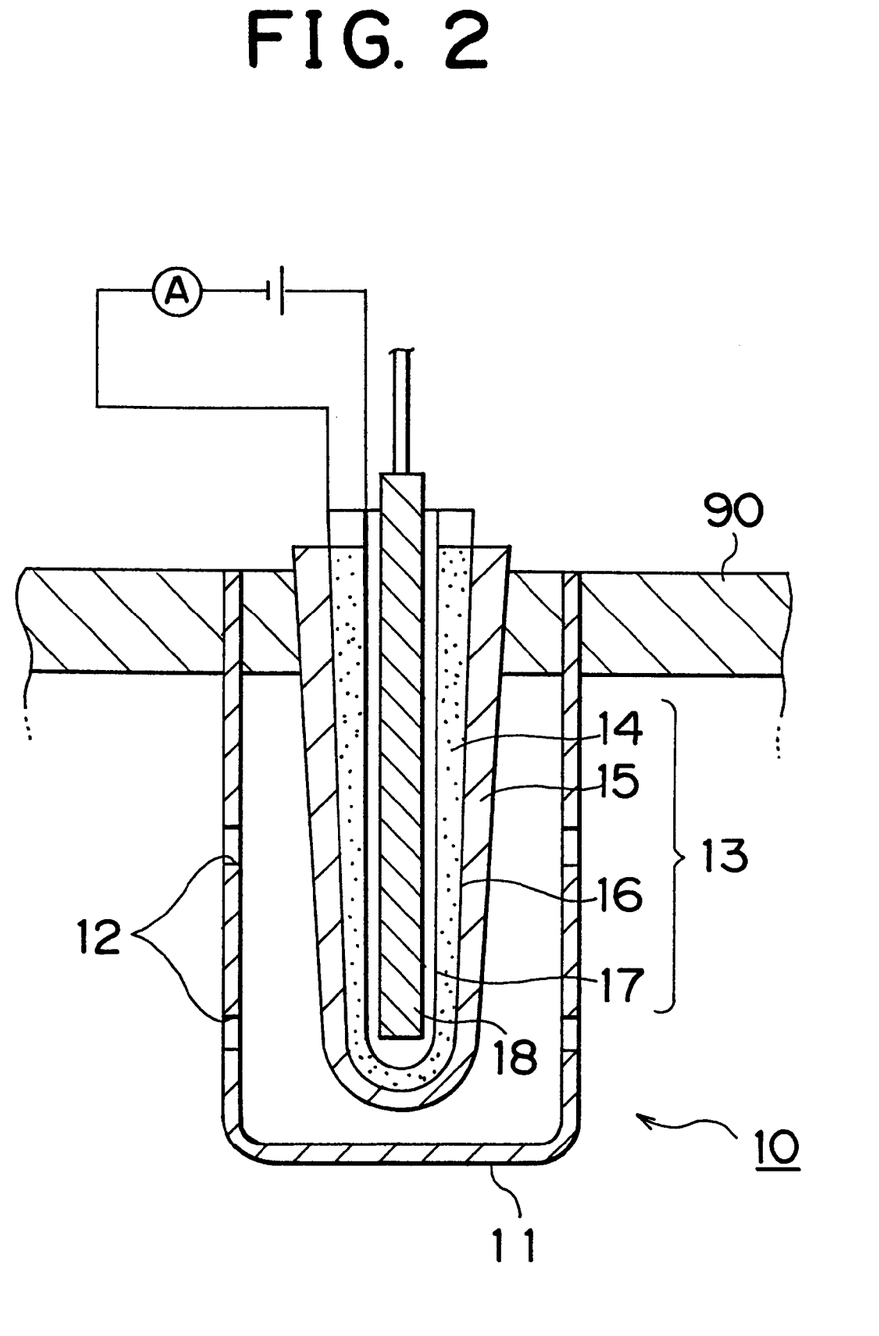
FIG. 2 is a sectional view of an example of an air-fuel ratio sensor.

FIG. 2 is a sectional view of an example of the air-fuel ratio sensor. An air-fuel ratio sensor 10 is protruded into an exhaust pipe 90 of an internal combustion engine. The air-fuel ratio sensor 10 is made up mainly of a cover 11, a sensor body 13, and a heater 18. The cover 11 has a cup-like sectional shape. A peripheral wall of the cover 11 has many small holes 12 for communication between the inside and the outside of the cover 11.

In the sensor body 13, an exhaust-side electrode layer 16 is fixed to an outer surface of an oxygen ion-conductive solid electrolyte layer 14 having a test tube-like shape. An atmosphere-side electrode layer 17 is fixed to an inner surface of the solid electrolyte layer 14. A diffusion resistance layer 15 is formed on an outer surface of the exhaust-side electrode layer 16 by plasma spraying or the like. In this embodiment, the solid electrolyte layer 14 is formed by a sintered oxygen ion-conductive oxide material in which CaO or the like is solid-dissolved as a stabilizer into $ZrO_2$ (zirconia element). The diffusion resistance layer 15 is formed by a heat-resistant inorganic material, such as alumina or the like. The exhaust-side electrode layer 16 and the atmosphere-side electrode layer 17 are each formed by a precious metal having a high catalytic activity, for example, platinum or the like, and are coated with a porous chemical plating or the like.

The heater 18 is disposed surrounded by the atmosphere-side electrode layer 17, for heating the sensor body 13 to activate the zirconia element 14. The heater 18 has a sufficiently large heat-producing capacity to activate the zirconia element 14.

The zirconia element 14 has a characteristic that when an oxygen concentration difference occurs across the element during a high-temperature activated state, the zirconia element 14 conducts oxygen ions ($O^{2-}$) from the higher-concentration side to the lower-concentration side. The zirconia element 14 has another characteristic that when an electric potential difference is applied across the zirconia element 14, the zirconia element 14 tends to cause migration of oxygen ions ($O^{2-}$) from the negative electrode to the positive electrode in accordance with the potential difference (oxygen pumping characteristic).

As indicated in FIG. 2, a constant bias voltage is applied between the atmosphere-side electrode layer 17 and the exhaust-side electrode layer 16 of the sensor body 13, with the atmosphere-side electrode layer 17 serving as a positive electrode and the exhaust-side electrode layer 16 serving as a negative electrode. When the exhaust air-fuel ratio is a lean ratio, oxygen ions ($O^{2-}$) migrate from the exhaust-side electrode layer 16 to the atmosphere-side electrode layer 17 due to the aforementioned oxygen pumping characteristic. As a result, a current flows from the positive electrode of a bias voltage source to the negative electrode of the bias voltage source, via the atmosphere-side electrode layer 17, the solid electrolyte layer 14 and the exhaust-side electrode layer 16. The magnitude of current thus produced corresponds to an amount of oxygen diffusing into the exhaust-side electrode layer 16 from exhaust gas via the diffusion resistance layer 15 provided that the bias voltage is equal to or higher than a predetermined constant value. Therefore, if the magnitude of this limit current is detected, an oxygen concentration can be determined from the detected magnitude of current, so that an air-fuel ratio in the lean range can be determined as described above with reference to FIG. 1.

When the exhaust air-fuel ratio is on the rich side, oxygen ions ($O^{2-}$) are caused to migrate from the atmosphere-side electrode layer 17 to the exhaust-side electrode layer 16 due to an oxygen battery characteristic. That is, the oxygen battery characteristic opposes the bias voltage. The air-fuel ratio sensor is designed so that the electromotive force created by the oxygen battery characteristic overcomes the bias voltage, so that a current flows from the atmosphere-side electrode layer 17 to the exhaust-side electrode layer 16 via the bias voltage source when the exhaust air-fuel ratio is on the rich side. The magnitude of current thus produced is determined by the amount of oxygen ions ($O^{2-}$) transported from the atmosphere-side electrode layer 17 to the exhaust-side electrode layer 16 via the solid electrolyte layer 14. Since oxygen ions thus transported to the exhaust-side electrode layer 16 are intended to react with (burn), in the exhaust-side electrode layer 16, unburned gas components, such as carbon monoxide, that diffuse into the exhaust-side electrode layer 16 from exhaust gas via the diffusion resistance layer 15, the amount of oxygen ions transported corresponds to the unburned gas concentration. Therefore, if the magnitude of this limit current is detected, an unburned gas concentration can be determined from the detected magnitude of current, so that an air-fuel ratio in the rich range can be determined as described above with reference to FIG. 1.

When the exhaust air-fuel ratio equals the stoichiometric air-fuel ratio, the amounts of oxygen and the unburned gas entering the exhaust-side electrode layer 16 achieve the chemical equivalent ratio, so that they completely react (burn) through the catalytic action of the exhaust-side electrode layer 16. Thus, the amount of oxygen in the exhaust-side electrode layer 16 becomes nil, that is, no oxygen ion to be transported based on the oxygen battery characteristic or the oxygen pumping characteristic occurs. Therefore, when the exhaust air-fuel ratio is the stoichiometric air-fuel ratio, no current occurs in the circuit.

Figure 3:
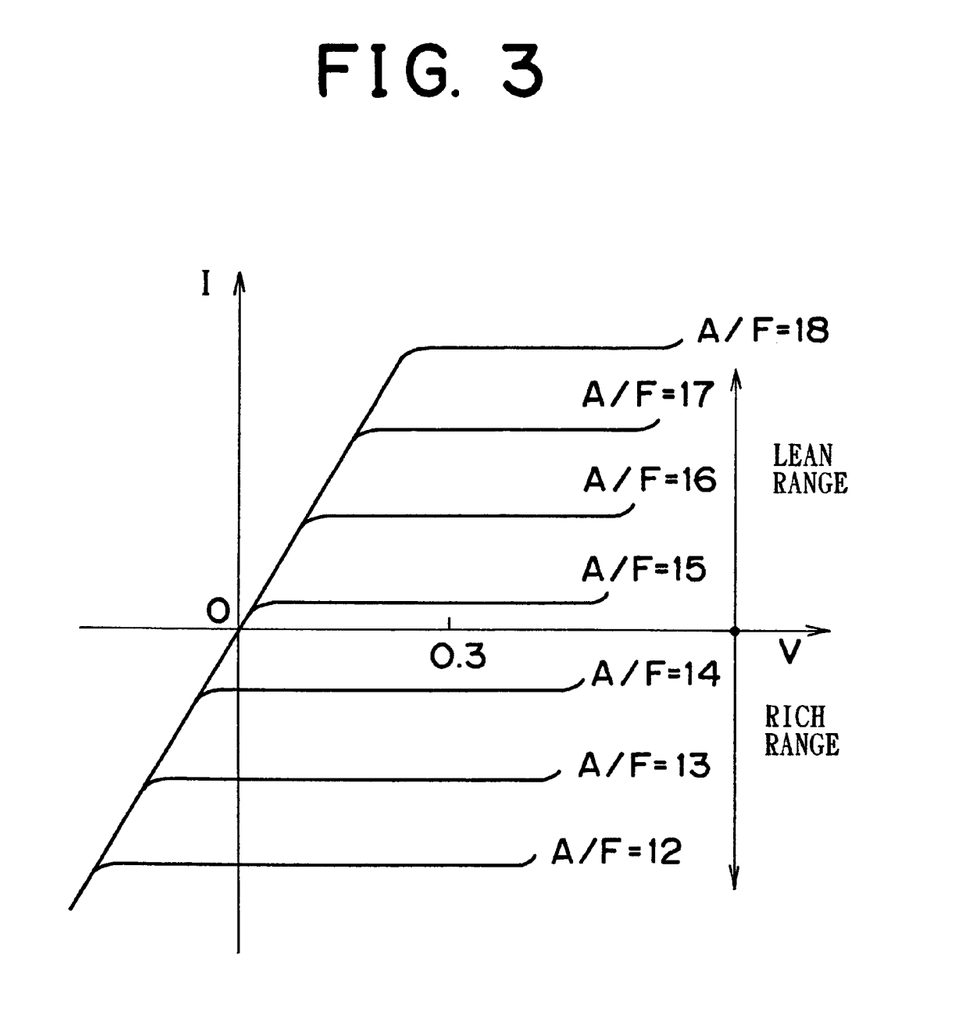
FIG. 3 is a characteristic graph indicating relationships between the exhaust air-fuel ratio and the output current of the air-fuel ratio sensor.

Therefore, the voltage-current (V-I) characteristic curves of the air-fuel ratio sensor indicate limit currents in accordance with the exhaust air-fuel ratios (A/F) to which the sensor is exposed, as shown in FIG. 3. In the graph of FIG. 3, linear portions of the characteristic curves parallel to the V-axis indicate limit currents. The direction of limit current in the lean range is opposite to the direction of limit current in the rich range. The absolute value of limit current increases as the air-fuel ratio increases within the lean range and decreases within the rich range. According to the characteristic curves in FIG. 3, air-fuel ratios from 12 to 18 can be detected if the applied voltage is set to about 0.3 V. A range of voltage below the linear portion of a curve indicating a limit current is a resistance-governed range.

An example of the hardware construction of the air-fuel ratio detecting apparatus will be described with reference to FIG. 4. The air-fuel ratio detecting apparatus is made up mainly of the air-fuel ratio sensor 10, a sensor body drive circuit 20, a heater drive circuit 30, and a central processing unit (CPU) 40. The air-fuel ratio sensor 10 includes the sensor body 13 and the heater 18 as described above with reference to FIG. 2. The heater drive circuit 30 receives a duty ratio signal and, in accordance with the duty ratio signal, applies the voltage of a battery 32 to the heater 18 in an on-off manner. The CPU 40 is provided as a central circuit of an electronic control unit (ECU) of an internal combustion engine for performing the fuel injection control, the ignition timing control, and the like. The CPU 40 contains an A/D converter (ADC), a D/A converter (DAC), and a memory.

The sensor body drive circuit 20 is made up mainly of a low-pass filter (LPF) 21, a first voltage follower 22, a reference voltage generating circuit 25, and a second voltage follower 26. The LPF 21 removes a high-frequency component from an analog signal outputted from the CPU 40. The first voltage follower 22 is equipped with an operational amplifier, a complementary push-pull amplifier, or the like. The first voltage follower 22 keeps the electric potential of the atmosphere-side electrode layer 17 of the sensor body 13 equal to the electric potential of the output of the LPF 21. This electric potential is 3.3 V at the time of air-fuel ratio detection.

The reference voltage generating circuit 25 generates a reference voltage of 3.0 V by dividing a constant voltage Vcc. The second voltage follower 26 has a circuit construction similar to that of the first voltage follower 22. The second voltage follower 26 keeps the electric potential of the exhaust-side electrode layer 16 of the sensor body 13 equal to the reference voltage of 3.0 V. Therefore, when an air-fuel ratio is to be detected, a voltage of 0.3 V is applied between the two electrode layers of the sensor body 13. Hence, the air-fuel ratio can be detected over a wide range by measuring limit current, as described above with reference to the characteristic diagram of FIG. 3. A resistor provided in the first voltage follower 22 functions as a current detecting circuit 23. The electric potentials at opposite ends of the resistor 23 are supplied to the CPU 40. The CPU 40 A/D-converts the analog potentials of the opposite ends of the resistor 23, and calculates an electric potential difference therebetween, and calculates a current from the potential difference and the resistance of the resistor 23.

Figure 5:
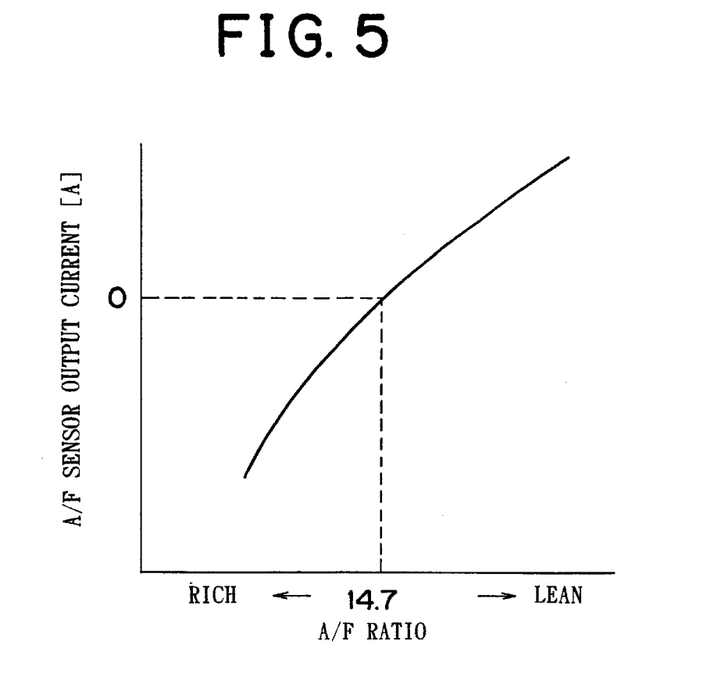
FIG. 5 is a characteristic graph indicating a relationship between the exhaust air-fuel ratio and the output current of the air-fuel ratio sensor.

As can be understood from the description with reference to FIG. 3, the calculated value of current and the exhaust air-fuel ratio have a relationship as indicated in FIG. 5. As a result, the CPU 40 can detect an exhaust air-fuel ratio based on a detected value of current and, therefore, can accomplish an air-fuel ratio feedback control.

Figure 6:
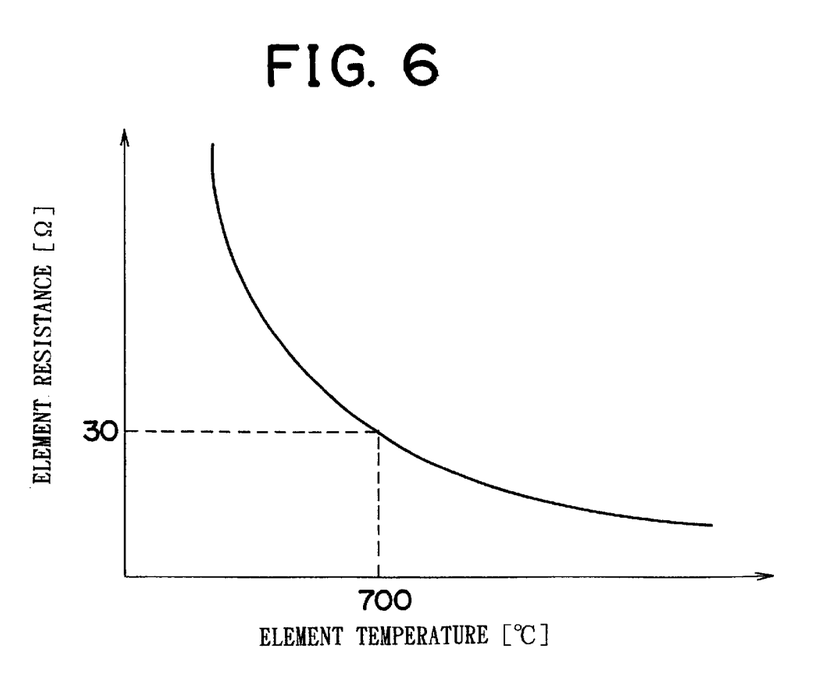
FIG. 6 is a characteristic graph indicating a relationship between the element temperature and the element resistance.

In order to detect an air-fuel ratio, it is necessary to maintain an active state of the oxygen ion-conductive solid electrolyte layer (element) 14. The active state thereof can be maintained by keeping the element 14 at a fixed temperature, for example, 700° C. The element temperature can be kept at 700° C. by maintaining an element resistance of 30 $\Omega$ because the element temperature and the element resistance have a certain correlation as indicated in FIG. 6. Therefore, a control of maintaining the active state of the element is performed by detecting an element resistance and performing a feedback control of the heater drive circuit 30 based on the detected value of element resistance.

Figure 7A:
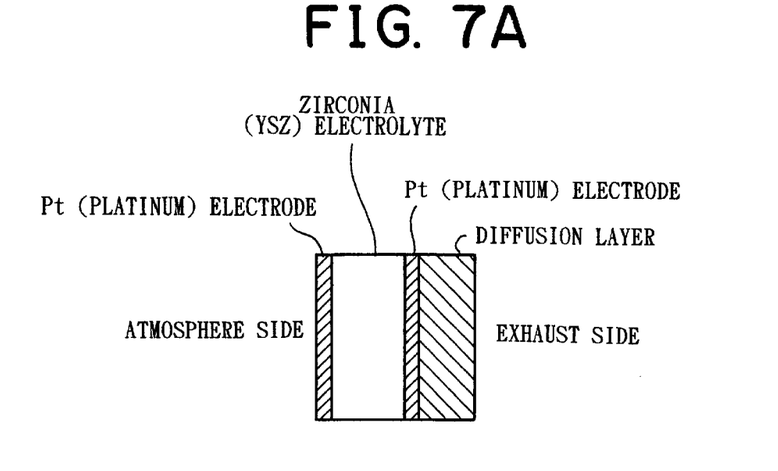
FIG. 7A is a sectional view illustrating the structure of a sensor body.
Figure 7B:
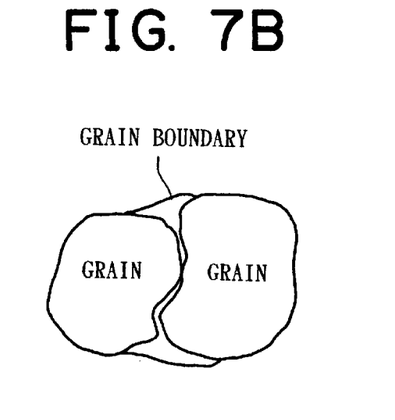
FIG. 7B is an enlarged fragmentary view of a solid electrolyte portion.
Figure 8:
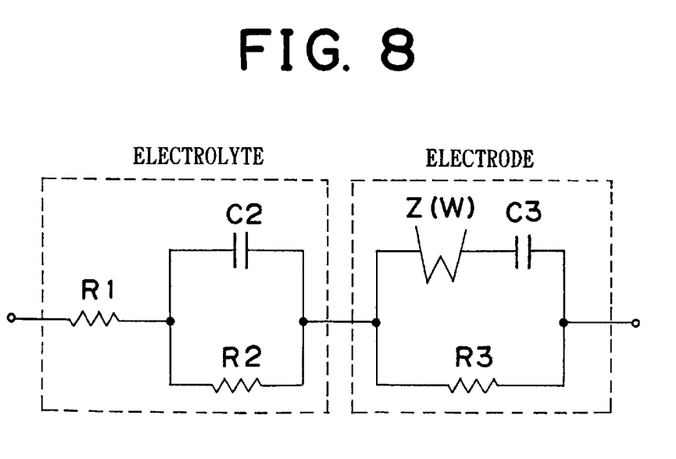
FIG. 8 is an equivalent circuit diagram of the sensor body.

FIG. 7A is a sectional view illustrating the structure of the sensor body 13. FIG. 7B is an enhanced fragmentary view of the solid electrolyte layer 14 of the sensor body 13. FIG. 8 is an equivalent circuit diagram of the sensor body 13. In the diagram of FIG. 8: R1 is a bulk resistance of a solid electrolyte made of, for example, zirconia, and corresponds to a grain portion as shown in FIG. 7B; R2 is a grain boundary resistance of the solid electrolyte and corresponds to a grain boundary as shown in FIG. 7B; R3 is an interface resistance of an electrode made of, for example, platinum; C2 is a capacitance component of the grain boundary of the solid electrolyte; C3 is a capacitance component of the electrode interface; and Z(W) is an impedance (Warburg impedance) caused by periodic changes in the interface concentration involved with polarization due to alternating currents.

As can be seen from FIG. 8, the resistance R1+R2+R3 can be detected if an output current of the sensor body 13 is measured by applying a voltage within the resistance-governed range (see FIG. 3) to the sensor body 13. However, the resistance R3 considerably changes due to deterioration of an electrode or the like, so that it is impossible to detect only the element resistance R1+R2. Furthermore, since the resistance-governed range varies in accordance with the air-fuel ratio as indicated in FIG. 3, it is very difficult to detect the element resistance based on the direct current characteristic of the sensor body 13. In order to deal with this problem, an element resistance detecting method utilizing an alternating current characteristic has been proposed.

Figure 9:
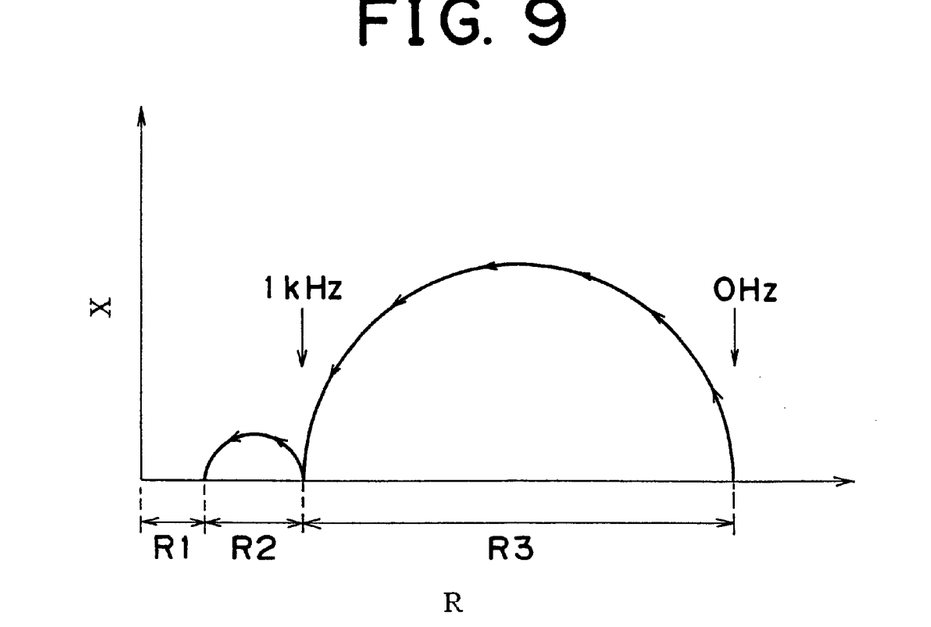
FIG. 9 is a diagram indicating a locus of the impedance of the sensor body formed in accordance with changes in the frequency of the input AC voltage superimposed on the air-fuel ratio-detecting DC voltage.

FIG. 9 is a diagram indicating a locus of the impedance of the sensor body that is formed in accordance with changes in the frequency f of the input AC voltage superimposed on the air-fuel ratio-detecting DC voltage (0.3 V). In the diagram, the horizontal axis indicates the real part R of the impedance Z, and the vertical axis indicates the imaginary part X thereof. The locus of the impedance does not depend on air-fuel ratio. The impedance Z of the sensor body is expressed as $Z=R+jX$. As indicated in FIG. 9, the impedance Z converges to the element resistance R1+R2 as the frequency f approaches 1 kHz.

Figure 10:
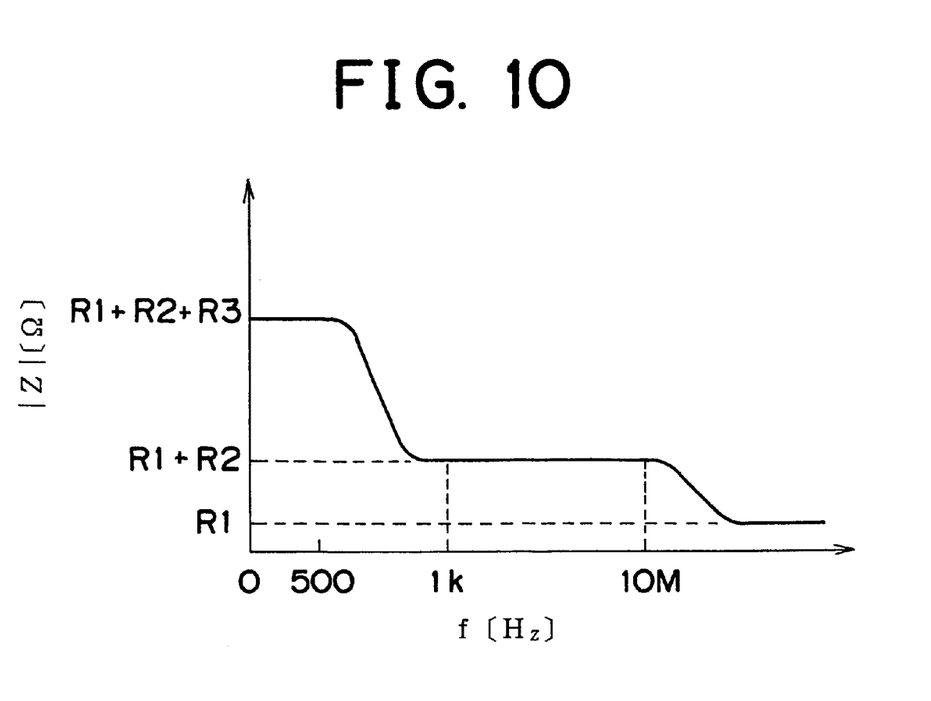
FIG. 10 is a graph indicating a relationship between the frequency of the input AC voltage and the element impedance.

FIG. 10 is a graph indicating a relationship between the frequency f of the input AC voltage and the absolute value |Z| of the impedance Z. It can be seen from FIG. 10 that |Z| substantially equals R1+R2 in the frequency range of 1 kHz to 10 MHz and that |Z| decreases and eventually converges to R1 in the high frequency range above 10 MHz. Therefore, it can be understood that a frequency approximately within the range of 1 kHz to 10 MHz is desirable in order to detect the element resistance R1+R2.

Figure 11A:
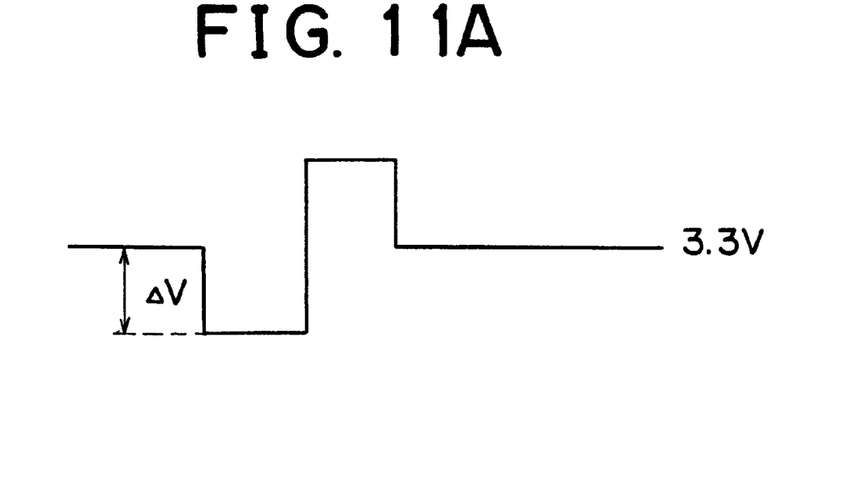
FIGS. 11A, 11B, 11C illustrate the waveform of input voltage to a low-pass filter, the waveform of input voltage to the atmosphere-side electrode of the air-fuel ratio sensor, and the waveform of output voltage of the air-fuel ratio sensor.
Figure 11B:
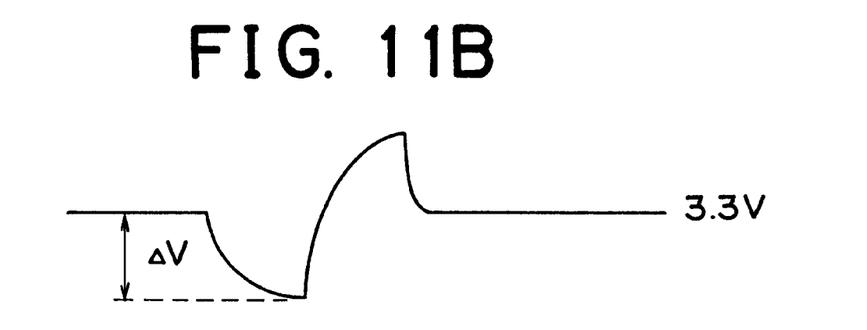
Figure 11C:
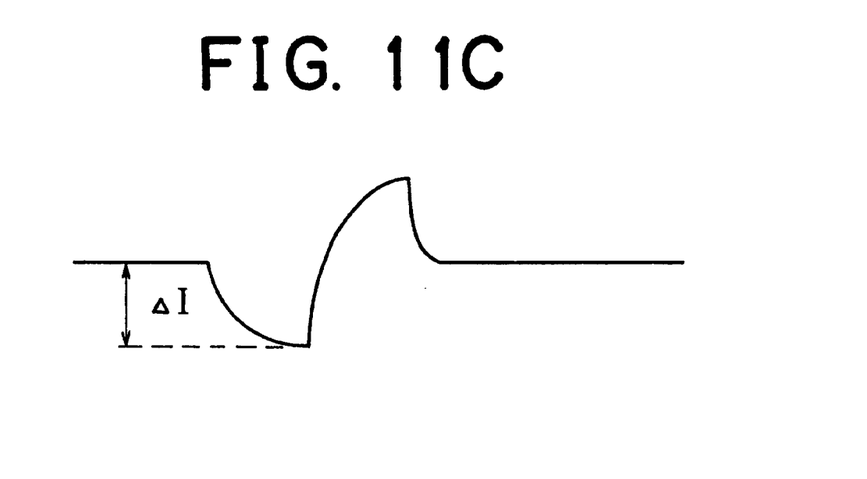

FIGS. 11A, 11B, 11C show the waveform of input voltage to the LPF 21, the waveform of output voltage from the LPF 21, that is, voltage applied to the atmosphere-side electrode layer 17 of the air-fuel ratio sensor 10, and the waveform of output voltage of the air-fuel ratio sensor 10.

In FIGS. 11A to 11C, the horizontal axis indicates time, and the vertical axis indicates voltage or current. As described above, the voltage to the exhaust-side electrode layer 16 is kept equal to the reference voltage of 3.0 V, and the voltage to the atmosphere-side electrode layer 17 is normally kept at 3.3 V as indicated in FIG. 11B. Therefore, the DC voltage normally applied between the electrodes of the air-fuel ratio sensor body is 0.3 V. The output DC current corresponding to the input DC voltage of 0.3 V indicates air-fuel ratio.

The CPU 40 changes the input voltage to the LPF 21 by $\Delta V$ as indicated in FIG. 11A in order to measure the element resistance. The voltage outputted from the LPF 21, that is, the voltage applied to the atmosphere-side electrode layer 17 of the air-fuel ratio sensor 10, has a waveform formed by superimposing, on the DC voltage of 3.3 V, an AC voltage pulse having a modified waveform and formed mainly by a component of a specific frequency (e.g., 5 kHz), as indicated in FIG. 11B. Corresponding to the AC voltage pulse, the output current changes by $\Delta I$ as indicated in FIG. 11C. An element impedance Z is given by $\Delta V/\Delta I$. By referring to the characteristic curve in FIG. 6 together with the given element impedance Z, an element temperature can be determined. The purpose of changing the applied voltage in both the decreasing direction and the increasing direction is to speed up the discharge of charges stored in the capacitance component.

Figure 4:
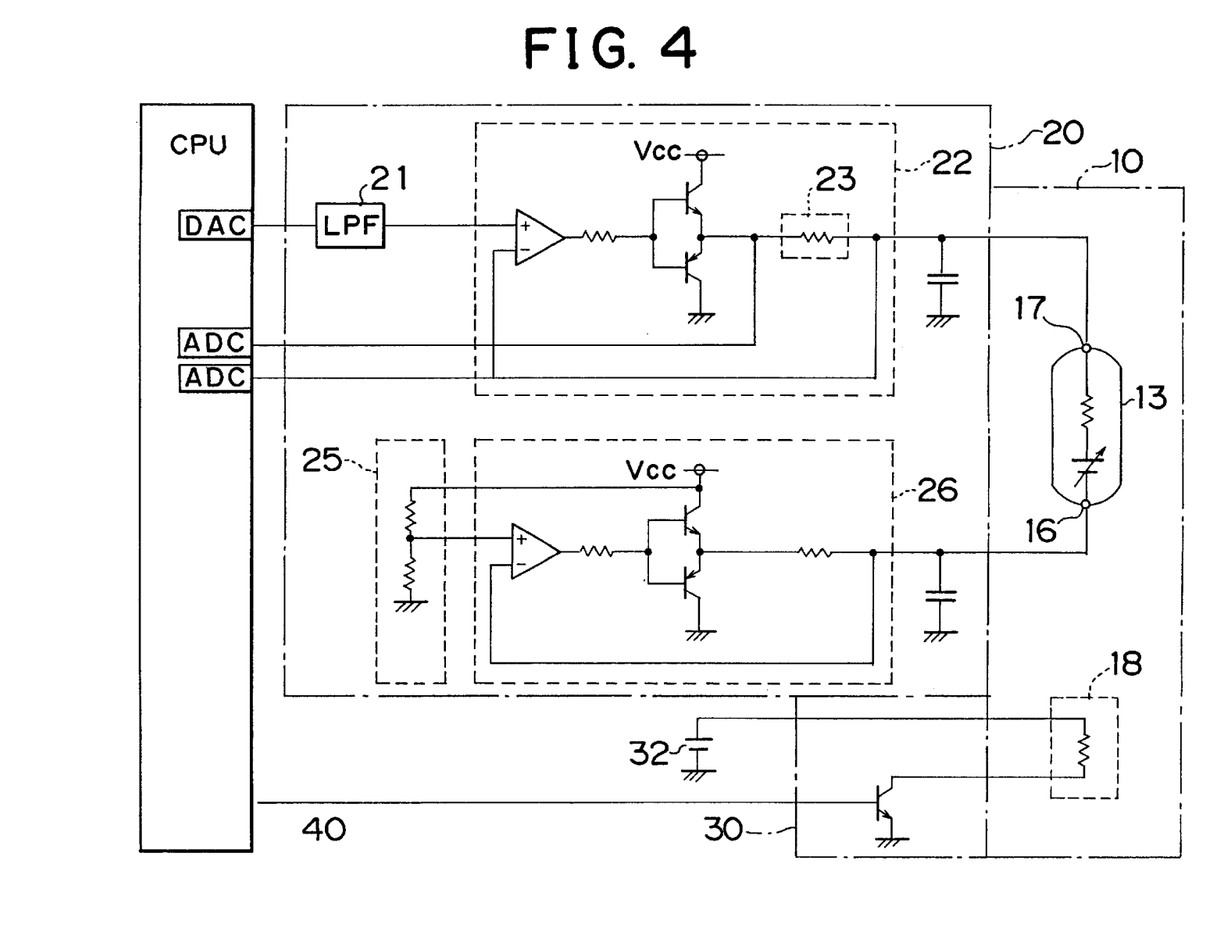
FIG. 4 is an electric circuit diagram illustrating a hardware construction of an air-fuel ratio detecting apparatus according to an embodiment of the invention.

It is considered that the air-fuel ratio detecting apparatus as shown in FIG. 4 is likely to have such a fault as a break in the sensor body 13 or the sensor body drive circuit 20, a break in the heater 18 or the heater drive circuit 30, deterioration of the heater 18, or the like. It is important to detect such faults in a simple, easy, and accurate manner.

A fault in which a wiring or the like breaks in the sensor body 13 or the sensor body drive circuit 20 so that a current does not flow through the circuit will be considered. If such a break occurs, it is difficult to determine whether the zero output current is a result of the break or a result of the exhaust air-fuel ratio actually equaling the stoichiometric air-fuel ratio. This determination becomes extremely difficult in a region in which the feedback control of the air-fuel ratio to the stoichiometric air-fuel ratio is performed. It is possible to consider a method that monitors variation of the output current in an air-fuel ratio control region in which some output current occurs. However, this method is not necessarily easy, because the setting of a threshold is difficult due to a detection error, differences among individual sensors, aging changes, noises, and other problems. Thus, the detection of a break in the sensor body 13 or the sensor body drive circuit 20 by utilizing the DC characteristic of the air-fuel ratio sensor has many problems.

In the invention, therefore, fault diagnosis is performed by utilizing the aforementioned AC characteristic of the air-fuel ratio sensor, that is, the aforementioned element impedance. The element impedance detected on the basis of the AC input-output characteristic as indicated in FIGS. 11B and 11C is not affected by air-fuel ratio. If there is a break in the sensor body 13 or the sensor body drive circuit 20, the output current of the circuit is always zero and exhibits no change, so that the calculated impedance becomes infinite. Therefore, the break can be easily detected.

Figure 12:
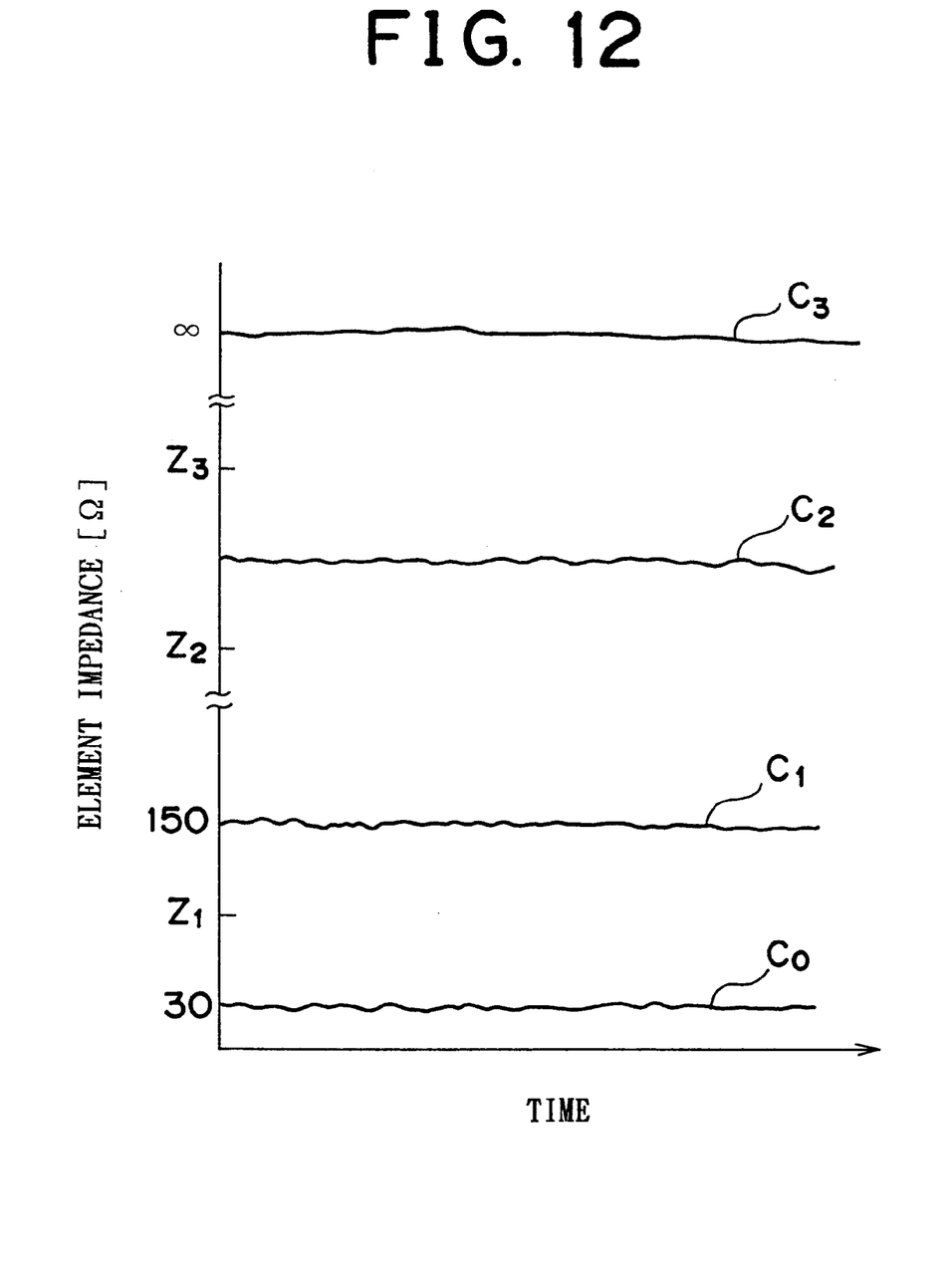
FIG. 12 is a time chart illustrating an example of the transition of element impedance over time.

Furthermore, since the element impedance reflects the element temperature as described above, utilization of the element impedance also makes it possible to detect a break in the heater 18 or the heater drive circuit 30 and detect deterioration of the heater 18. FIG. 12 is a chart illustrating an example of the transition of the element impedance over time during the active state of the element. When there is no fault or the like, the element temperature is about 700° C., so that the element impedance becomes a sufficiently low value of about 30 Ω as indicated by a curve $C_0$. If there is a break in the sensor body 13 or the sensor body drive circuit 20, the detected element impedance becomes infinite as indicated by a curve $C_3$.

If the heater 18 has deteriorated, the element temperature rises only up to, for example, about 550° C. despite sufficient electrification of the heater 18, so that the element impedance becomes only about 150 Ω as indicated by a curve $C_1$. If there is a break in the heater 18 or the heater drive circuit 30, the element is heated only by exhaust gas, so that the element temperature rises only up to about the temperature of exhaust gas (about 300° C.). Therefore, the element impedance becomes a value corresponding to an element temperature of 300° C. as indicated by a curve $C_2$.

Therefore, if three reference values (thresholds) Z1, Z2, Z3 are set as indicated in FIG. 12, and compared with the detected value of element impedance, it becomes possible to determine whether there is a break in the sensor body 13 or the sensor body drive circuit 20, or a break in the heater 18 or the heater drive circuit 30, or deterioration of the heater 18, or no fault.

Figure 13:
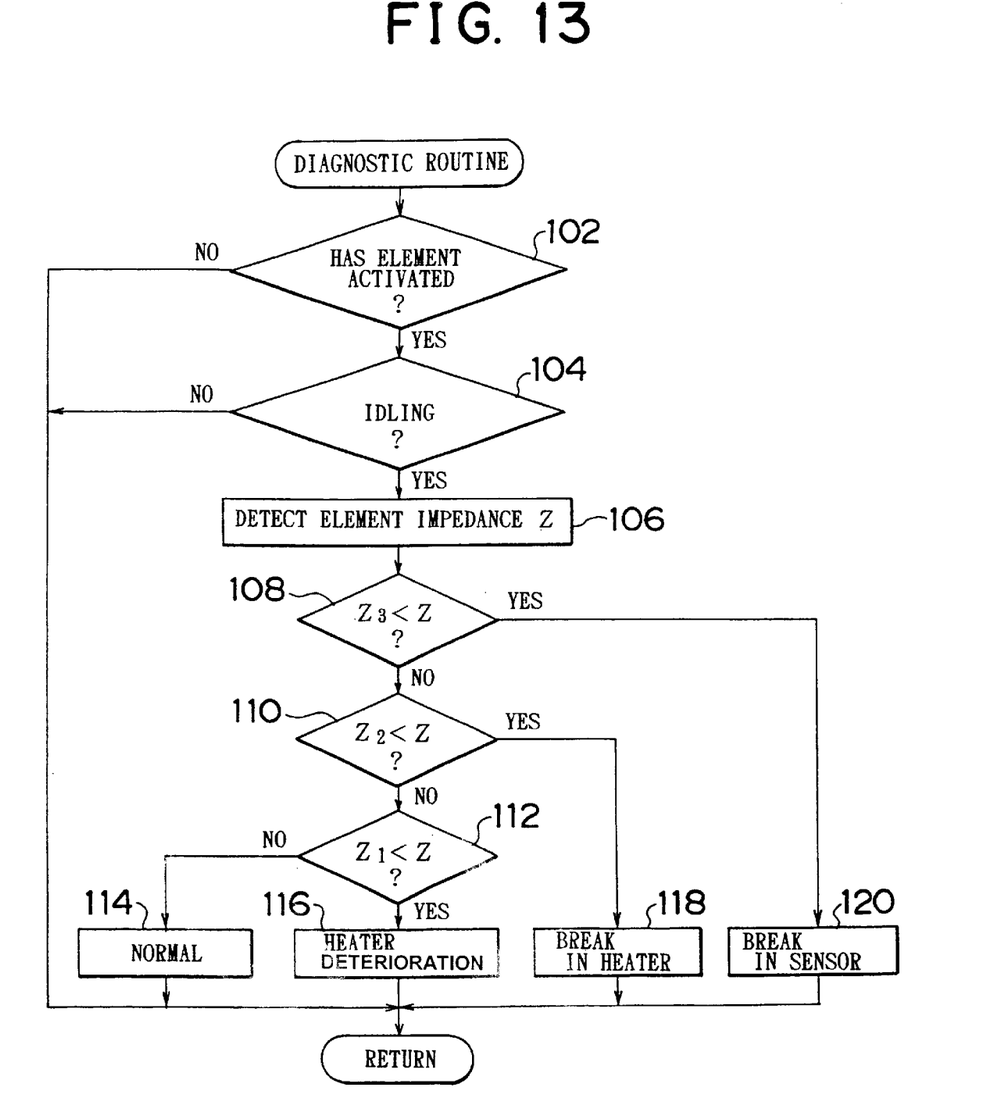
FIG. 13 is a flowchart illustrating the procedure of a fault diagnostic routine executed by a CPU.

FIG. 13 is a flowchart illustrating the procedure of a fault diagnostic routine executed periodically by the CPU 40. In step 102, the CPU 40 determines whether the element is in the active state on the basis of the elapsed time following a startup of the engine. If the element has activated, the process proceeds to step 104. Conversely, if the element is not in the active state, the CPU 40 ends this execution of the routine. The determination as to whether the element has activated becomes unnecessary if only a break in the sensor body 13 or the sensor body drive circuit 20 is to be detected.

In step 104, the CPU 40 determines whether the internal combustion engine is idling on the basis of a completely closed throttle signal, a vehicle speed signal and the like. If the engine is idling, the process proceeds to step 106. Conversely, if the engine is not idling, the CPU 40 ends the execution of the routine. The processing in step 104 is not essential but is merely provided considering that if the engine is idling, the exhaust gas temperature, that is, one factor of the heating of the element, becomes stable and, therefore, the diagnostic precision improves.

In step 106, the CPU 40 detects an element impedance Z by superimposing an AC voltage pulse on the input DC voltage and measuring an output AC current pulse as described above with reference to FIGS. 11A to 11C. Subsequently in steps 108, 110, 112, the CPU 40 performs diagnosis by comparing the detected element impedance Z with the three reference values Z1, Z2, Z3 indicated in FIG. 12.

That is, if $Z \leq Z1$, it is determined in step 114 that there is no fault. If $Z1 < Z \leq Z2$, it is determined in step 116 that the heater 18 has deteriorated. If $Z2 < Z \leq Z3$, it is determined in step 118 that there is a break in the heater 18 or the heater drive circuit 30. If $Z3 < Z$, it is determined in step 120 that there is a break in the sensor body 13 or the sensor body drive circuit 20.

While the present invention has been described with reference to what is presently considered to be a preferred embodiment thereof, it is to be understood that the invention is not limited to the disclosed embodiment or constructions. To the contrary, the invention is intended to cover various modifications and equivalent arrangements.

What is claimed is:

1. An air-fuel ratio detecting apparatus comprising:
   an air-fuel ratio sensor having a sensor body which, upon application of a voltage to the sensor body, generates a limit current in accordance with at least one of an oxygen concentration and an unburned gas concentration in a detection-object gas;
   a sensor body drive circuit that drives the sensor body;
   element impedance detection means for detecting an impedance of an oxygen ion-conductive element provided in the sensor body by applying an AC voltage to the sensor body; and
   diagnostic means for detecting and diagnosing faults based on the detected element impedance.

2. An apparatus according to claim 1, wherein, when the element impedance is greater than a first reference value, the diagnostic means determines that there is a break in at least one of the sensor body and the sensor body drive circuit.

3. An apparatus according to claim 1, wherein the air-fuel ratio sensor has a heater that heats the sensor body to activate the oxygen ion-conductive element, the air-fuel ratio detecting apparatus further comprising a heater drive circuit that drives the heater, and wherein, when the element impedance is smaller than a first reference value but greater than a second reference value, the diagnostic means determines that there is a fault in at least one of the heater and the heater drive circuit.

4. An apparatus according to claim 3, wherein, when the element impedance is smaller than a third reference value that is between the first and second reference values and the element impedance is greater than the second value, the diagnostic means determines that the heater has deteriorated.

5. An apparatus according to claim 3, wherein, when the element impedance is greater than a third reference value that is between the first and second reference values and the element impedance is smaller than the first value, the diagnostic means determines that there is a break in at least one of the heater and the heater drive circuit.

6. An apparatus according to claim 1, wherein the diagnostic means diagnoses faults when the oxygen ion-conductive element is in an active state.

7. An apparatus according to claim 1, wherein the diagnostic means diagnoses faults when an internal combustion engine in which the air-fuel ratio sensor is installed is in an idle state.

8. An apparatus according to claim 1, wherein the element impedance detection means detects the element impedance by applying a voltage to the sensor body, wherein the voltage includes an element impedance-detecting AC component superimposed on an air-fuel ratio-detecting DC component, and measures an AC component of an output current of the air-fuel ratio sensor.

9. A control method for an air-fuel ratio detecting apparatus including an air-fuel ratio sensor having a sensor body that generates a limit current in accordance with at least one of an oxygen concentration and an unburned gas concentration of a detection-object gas upon application of a voltage to the sensor body, and a sensor body drive circuit that drives the sensor body, the method comprising the steps of:
   detecting an element impedance of an oxygen ion-conductive element provided in the sensor body by applying an AC voltage to the sensor body; and
   detecting and diagnosing faults based on the element impedance detected by the element impedance detection means.

10. A method according to claim 9, wherein, when the element impedance is greater than a first reference value, it is determined that there is a break in at least one of the sensor body and the sensor body drive circuit.

11. The method of claim 9, wherein the air-fuel ratio sensor has a heater that heats the sensor body to activate the oxygen ion-conductive elements the air-fuel ratio detecting apparatus further comprising a heater drive circuit that drives the heater, and wherein, when the element impedance is smaller than a first reference value but greater than a second reference value, the diagnostic means determines that there is a fault in at least one of the heater and the heater drive circuit.

12. A method according to claim 11, wherein, when the element impedance is smaller than a third reference value that is between the first and second reference values and the element impedance is greater than the second value, it is determined that the heater has deteriorated.

13. A method according to claim 11, wherein, when the element impedance is greater than a third reference value that is between the first and second reference values and the element impedance is smaller than the first value, it is determined that there is a fault in at least one of the heater and the heater drive circuit.

14. A method apparatus according to claim 9, wherein diagnosis is performed when the oxygen ion-conductive element is in an active state.

15. A method according to claim 9, wherein diagnosis is performed when an internal combustion engine in which the air-fuel ratio sensor is installed is in an idle state.

16. A method according to claim 9, wherein the element impedance is detected by applying a voltage to the sensor body, the voltage including an element impedance-detecting AC component superimposed on an air-fuel ratio-detecting DC component, and measuring an AC component of an output current of the air-fuel ratio sensor.

* * * * *